(12) United States Patent
Mettier et al.

(10) Patent No.: US 9,321,048 B2
(45) Date of Patent: Apr. 26, 2016

(54) SAMPLE DISTRIBUTION SYSTEM AND PROCESS

(71) Applicant: Integra Biosciences AG, Zizers (CH)

(72) Inventors: Ivo Mettier, Felsberg (CH); Richard Larry Keene, Andover, MA (US)

(73) Assignee: Integra Biosciences AG (CH)

( * ) Notice: Subject to any disclaimer, the term of this patent is extended or adjusted under 35 U.S.C. 154(b) by 300 days.

(21) Appl. No.: 13/967,481

(22) Filed: Aug. 15, 2013

(65) Prior Publication Data

US 2014/0047931 A1    Feb. 20, 2014

(30) Foreign Application Priority Data

Aug. 15, 2012    (CH) ...................................... 1365/12

(51) Int. Cl.
| | |
|---|---|
| *G01N 1/22* | (2006.01) |
| *B01L 3/02* | (2006.01) |
| *B01L 9/00* | (2006.01) |
| *G01N 35/10* | (2006.01) |
| *G01N 35/00* | (2006.01) |

(52) U.S. Cl.
CPC .............. *B01L 3/021* (2013.01); *B01L 3/0237* (2013.01); *B01L 9/54* (2013.01); *G01N 35/00871* (2013.01); *G01N 35/1011* (2013.01); *B01L 2200/028* (2013.01); *B01L 2300/023* (2013.01); *G01N 35/1065* (2013.01)

(58) Field of Classification Search
CPC ..................... G01N 35/00732; G01N 35/0099; G01N 35/026; G01N 35/04; G01N 35/1011
USPC ....................................................... 73/863.01
See application file for complete search history.

(56) References Cited

U.S. PATENT DOCUMENTS

| | | |
|---|---|---|
| 5,343,769 A | 9/1994 | Suovaniemi et al. |
| 5,415,060 A | 5/1995 | DeStefano, Jr. |
| 6,778,917 B1 | 8/2004 | Jansen |

(Continued)

FOREIGN PATENT DOCUMENTS

| | | |
|---|---|---|
| DE | 10 2008 010 267 | 8/2009 |
| EP | 0 864 364 | 9/1998 |
| WO | 2012/069925 | 5/2012 |

*Primary Examiner* — Peter Macchiarolo
*Assistant Examiner* — Mohammed E Keramet-Amircolai
(74) *Attorney, Agent, or Firm* — Andrus Intellectual Property Law, LLP

(57) ABSTRACT

On the one hand the invention relates to a distribution apparatus 41 for hand held distribution of fluid samples with a data carrier and a first communication interface. On the other hand it concerns a positioning device 21 comprising a first holder 23 adapted for holding the distribution apparatus 41, a second holder 25 adapted for holding a target container 63, an actuator for effecting a relative movement of the first and the second holder 23, 25, and a second communication interface. These two components are part of a sample distribution system 11 which is also subject matter of the invention, including its use in a process for sample distribution. A relevant aspect of the invention is that the data carrier of the distribution apparatus contains information determining the operation of the actuator. The first and the second communication interfaces are configured for the transmission of said information from the distribution apparatus 41 to the positioning device 21, and the positioning device 21 is configured for effecting operation of the actuator as determined by the information.

21 Claims, 2 Drawing Sheets

(56) References Cited

U.S. PATENT DOCUMENTS

2003/0152493 A1* 8/2003 Lefebvre .................. 422/100
2009/0274587 A1* 11/2009 Butz et al. ................ 422/100
2011/0209564 A1* 9/2011 Von Beichmann
 et al. ..................... 73/864.01
2011/0268627 A1 11/2011 Warhurst et al.
2011/0296931 A1* 12/2011 Warhurst ............... 73/864.01

* cited by examiner

SAMPLE DISTRIBUTION SYSTEM AND PROCESS

FIELD OF THE INVENTION

The invention relates to a positioning device, a hand held distribution apparatus removably mountable in the positioning device, a sample distribution system with a positioning device and a distribution apparatus, and a sample distribution process which makes use of said system.

BACKGROUND OF THE INVENTION

Hand held distribution apparatuses are known in the art as useful tools in laboratories. They are mainly used for distributing one or more samples to a target container, for example a plate with a plurality of wells. There are hand-operated dispensers and pipettes including single-channel (having a single release channel) and multi-channel (having several release channels) devices as described for example in application US 2009/0274587 A1. Their release channels allow the release and normally also the uptake of fluid samples.

Pipettors (also called pipettes), as the distribution apparatuses of primary interest in the context of this application, are understood to be devices used to transport a measured volume of liquid. The sample volume, which is released by the device by a single operation, may (substantially) correspond to the sample volume aspirated into the device. However, there are also pipettes that are capable of aspirating a measured volume of liquid and then releasing measured partial volumes (of the aspirated volume) by single operations. In this case the aspirated sample volume corresponds to several release doses and is therefore released stepwise.

Electronic versions of such devices are also known. They are often programmable either manually via a user interface or via a data interface that may be connected to a computer (see for example U.S. Pat. Nos. 6,778,917 B1 and 5,343,769, European application EP 0 864 364 A4 The programming either contributes to the control of the device's operation or it allows for data collection during operation. Operating such distribution apparatuses normally includes moving the apparatus manually from the source container where the sample is aspirated to the target container where it is released. Target containers often contain a multitude of receptacles that need to be filled in sequence which requires a considerable number of operations. The process is thus prone to errors and requires a lot of hand work.

Automated pipetting apparatuses as described for example in US applications 2011/0268627 A1 or US 2011/0296931 A1—that perform the aspiration of samples at the source container, their transfer to the target container, and the release of the samples to the correct part of the target container (e.g. a certain number of wells) allow for higher precision and increased throughput. However, such robots are expensive pieces of laboratory equipment and often difficult to operate since programming them is a rather complex task. They are either fully automated or semi-automated. Robots with a semi-automated mode of operation like those described in US 2011/0268627 A1 and US 2011/0296931 A1 may be manually directed by controls installed on the device like buttons, wheels, or a control handle. As a consequence of their automated nature they require less or no it from the operator once they have been programmed. However, they are stationary and thus less versatile than hand-held devices.

WO 2012/069925 A1 describes a fully automated programmable robot that utilizes hand-held mechanical pipettes. The pipettes may be removed from the robot and operated by hand. Due to the fact that the robot needs to be capable of performing all process steps otherwise carried out by a human operator it is by nature complex and expensive. As a result, devices of intermediate complexity have been developed like the one taught in U.S. Pat. No. 5,415,060 which comprises a movable holder for a well plate and a fixed support bridge for supporting a pipettor. The distribution system according to US 2011/0209564 A1 improves on the aforementioned device and further comprises a mechanism for guiding the operator's hand during sample distribution and thereby increases precision. The latter document teaches a positioning device adapted for holding a manually operated distribution apparatus (pipettor or dispenser) and a target container. The distribution apparatus in its mounted state is movable relative to the target container. The relative movement is however limited wherein the limitation is adjusted automatically upon each distribution step. Thus the device takes over the decision of the person using a manually operated distribution apparatus to decide which target position on a well plate has to be approached next. The means for limiting movement, which are part of the positioning device, can provide electrical control components, such as circuits and programmable digital or analogue controls. It is also mentioned that the sample distribution system may be semi- or fully automated and/or a robot and that it may be operated semi- or fully automatically, electrically, hydraulic, pneumatic etc. However, few details are provided in this respect since the document focuses on a manually actuable apparatus which is preferably usable without an external electrical energy source. A device as described in US 2011/0209564 A1 still requires the operator's presence and attention. This also applies to the device disclosed in DE 10 2008 010 267 A1 which teaches an apparatus similar to the one taught in US 2011/0209564. The apparatus comprises a locking bar with periodical locking positions and a marking unit which is movable at a guide and has a marking pin to fix the bar at one locking position. A marking position is indicated at a marking element or a slider and a coupling unit has a coupling pin for fixing the position of the pipette unit in the slider at the marking unit in the marking position. The mechanism thus guides the operator's hand during sample distribution, by restricting its freedom of movement. It is also mentioned that the apparatus may be automatic or semi automatic and may for this purpose comprise a number of electronic or electric components. Since they are described as parts of the stationary guiding device this would make the apparatus a robot like the ones described above with the exception that the programming and control of the automated variant of the device taught in DE 10 2008 010 267 A1 is performed on and by a computer connected to the apparatus via an interface.

OBJECT OF THE INVENTION

It is an object of the present invention to provide an improved liquid skimp! distribution system and process. In particular the invention aims at providing a distribution system that is optimized regarding the parameters complexity, price, throughput, and precision. On the one hand, it should be less complex and thus less expensive than a fully automated sample distribution robot. On the other hand, substantially improved precision and throughput should be achieved compared to manually operated distribution apparatuses.

DESCRIPTION OF INVENTION

The above mentioned object can be achieved by a sample distribution system according to claim 1 or more generally a sample distribution system comprising a distribution apparatus for distribution of fluid samples (i.e. volumes of fluid) and a positioning device. The positioning device comprises a first holder adapted for (removably) holding the distribution apparatus and a second holder adapted for (removably) holding a target container wherein the first and the second holder are movable relative to each other. Furthermore, the positioning device is configured for receiving information determining the relative movement of the first and second holder from the distribution apparatus.

According to an embodiment of the invention a distribution apparatus like a hand-held electronic pipettor which can be operated independent of a positioning device and/or by hand is mounted in the holder of a positioning device and controls the movement of the said holder relative to a target container and/or relative to the rest of positioning device.

The fact that the distribution apparatus is capable of controlling the positioning device (or at least the part of it that effects the relative movement of the holders) results in a number Of advantages, in particular if the distribution apparatus also controls itself (or at least the part of itself that effects release and/or uptake of samples).

Firstly, the positioning device may be constructed in a simple and inexpensive way as opposed to the use of a complex robotic manipulator with a vision system as e.g. described in WO 2012/069925 A1. In an embodiment of the present invention the positioning device is merely an accessory for a distribution apparatus and does thus not require complicated programming and a user interface suitable for carrying out such programming. Secondly, existing electronic pipettors—as for example the one described in US 2009/0274587 A1—may act as distribution apparatuses according to the invention after only minor adjustments (programming, communication interface). Thirdly, a user does not need to be present for sample distribution since the distribution apparatus and the positioning device can both be controlled by the distribution apparatus resulting in a coordinated operation of the two devices. Fourthly, if the entry, alteration, or selection of the information determining the operation of the positioning device and/or the distribution apparatus is carried out before mounting the distribution apparatus in the first holder of the positioning device efficiency is increased since users do not have to wait until the positioning device is no longer occupied to prepare the programming. Furthermore, they may also prepare other parts of the distribution apparatus (replacing tips etc.) in advance. Fifthly, the distribution apparatus remains independently manually operable (whereas the positioning device requires a distribution apparatus for sample distribution). Consequently, one or more steps of the distribution process, like aspiration, may be carried out manually using only the distribution apparatus and the rest may be carried out automatically with the help of the positioning device.

In the following, preferred embodiments of the invention are described. The features mentioned in respect of said embodiments are to be (individually) considered preferred features and they may be implemented individually or in any combination provided such features do not exclude each other.

According to a preferred embodiment of the invention the sample distribution system comprises
- a distribution apparatus for hand held distribution of fluid samples which comprises a data carrier and preferably a first communication interface, and
- a positioning device which comprises a first holder adapted for holding the distribution apparatus, a second holder adapted for holding a target container, an actuator for effecting a relative movement of the first and the second holder, and preferably a second communication interface, wherein
- the data carrier contains information determining (some or all of) the operation of the actuator (and/or of other parts of the positioning device),
- the first and the second communication interfaces are preferably configured for the direct or indirect transmission of the information from the distribution apparatus to the positioning device, and
- the positioning device is configured for receiving the information from the distribution apparatus and for effecting operation of the actuator (and/or other parts of the positioning device) as determined by the information.

In another aspect of the invention the distribution apparatus is preferably programmable. According to a preferred embodiment the distribution apparatus is a hand held and/or manually operated pipettor, in particular an electronic pipettor. The distribution apparatus may be a pipettor with 1 to N channels (typically 8, 12 or 16 channels). Furthermore, it may be a pipettor with fixed channels or a pipettor that allows for the distance between neighboring channels to be changed via an actuator (e.g. a pipettor as described in US2009/027458 A1 whose content is here with incorporated by reference).

According to one embodiment, the distribution apparatus can be connected via a wired or wireless communication interface (e.g. via USB) to a computer. Information may be entered on the computer and transmitted via the above mentioned interface to the distribution apparatus and/or vice versa. Furthermore, the computer may be used to control the distribution apparatus and/or the positioning device remotely or to provide them with upgraded firmware. The input via a computer is however primarily useful for information in the form of programs.

It is preferred that the distribution apparatus comprises a user interface configured for manual entry, selection and alteration of the information determining the operation of the positioning device and the actuator respectively (and preferably also of the distribution apparatus itself). The user interface may comprise a display and controls (e.g. buttons, wheels, halls etc.). Furthermore, it is preferred that the distribution apparatus provides a graphical user interface.

The distribution apparatus is a device that can be used for sample distribution independently of other devices including the positioning device. During such hand held and/or manual sample distribution the distribution apparatus is normally moved and/or lifted by hand from a source container (preferably a reservoir) to a target container (preferably a multi-well-plate). Preferably, this applies to the entire device, or at least the greater part thereof in terms of weight. In contrast, the positioning device preferably requires a distribution apparatus to be mounted in the first holder for carrying out the sample distribution process.

The data carrier is preferably a non-volatile data storage device like a flash memory chip. According to an embodiment of the invention it is part of the distribution apparatus and may be positioned in or on the distribution apparatus. It may or it may not be removable from the distribution apparatus.

If reference is made in this document (except for the claims) to the "information" there shall also be disclosed in part of said information and a precursor of the information provided this makes sense in the respective context. The reason is the following: The information which is transmitted from the distribution apparatus to the positioning device may be derived from data entered, altered, selected or assembled by the user and/or stored on the data carrier of the distribution apparatus. In other words, this data may be processed and thus altered before the transmission to the positioning device and again after it has arrived at the positioning device. Consequently, the entered data may be a precursor or only part of the transmitted data. Relevant is that the information transmitted from the distribution apparatus to the positioning device contains—in whatever form—parameters, programs, program parts, and/or signals etc. that determine and/or control the operation of the positioning device or part thereof, in particular the operation of the actuator. The information is preferably present in the form of data, e.g. as files.

Furthermore, if in this document (except for the claims) reference is made to the "information" the information determining the operation of flu positioning device is meant except where a different kind of information is specified. However, it is preferred that the operation of the distribution apparatus or part thereof (in particular the uptake and release of samples while held by the first holder) is also determined by information stored on the data carrier. All features (concerning entry, alteration, selection, storage etc.) mentioned in this document in respect of the information determining the operation of the positioning device shall also be disclosed for the information determining the operation of the distribution apparatus except for the fact that it has another purpose (preferably it determines/controls the uptake and release of samples) and does not have to be transmitted to the positioning device. It is further preferred that the positioning device provides the distribution apparatus with information indicating the status of the positioning device (e.g. the position of the holders, whether the distribution apparatus is correctly mounted in the first holder etc.). Such status information may also be transmitted via the communication interfaces described in this document, stored on the data carrier of the distribution apparatus and if necessary displayed via the user interface of the distribution apparatus.

Of particular interest is a hand held programmable, electronic pipettor removably mounted in an instrument wherein the pipettor operation and the instrument operation are coordinated, together to effect fluid distribution between a source container and a target container.

In a preferred embodiment the first holder and the second holder are movable relative to each other in a first and a second direction to allow samples to be transferred from the distribution apparatus to the target container or predetermined parts of the target container. Preferably, the movement also allows samples to be transferred from a source container to the target container and/or from one part of the target container to another part thereof.

It is preferred that the movements in the first and the second direction are (substantially) linear movements even though essentially any kind of movement is possible (provided the starting and endpoint are the same). Furthermore, the first direction is preferably perpendicular to the second direction.

In another aspect of the invention the first holder and the second holder are also movable relative to each other in a third direction. Again this movement is preferably linear. Furthermore, it is preferred that the third direction is perpendicular to the first and/or the second direction.

The aspiration of fluid into the distribution apparatus may be effected manually before placing the distribution apparatus in the first holder. However, it is advantageous if the positioning device comprises a third holder for holding a source container. Like the target container the source container may comprise one or more sample receptacles or wells which are separated/isolated from each other (e.g. 6, 12, 24, 48, 96 or 384). Thus it may hold one or more different fluids. Normally, however, the source container is a reservoir with less than 20 (preferably 16), less than 10 or less than 5 and preferably just one receptacle(s) or well(s).

According, to another aspect of the invention, the first holder and the second holder and/or the first holder and the third holder are moveable relative to each other in a first and a second direction to allow samples to be transferred from the source container to the target container. These relative movements should allow for the distribution apparatus to be positioned above the source container to permit the aspiration of fluid and also above the target container to permit the release of the fluid thereto. There are a number of ways to achieve this result. In principle any one of the holders could be immobile if the other two holders were movable. However, since the source container normally contains more liquid than the target container it is preferably immovable relative to the positioning device to prevent spillage caused by motion.

It is preferred that the movement in one (preferably the first) direction is an up-and-down movement, in particular a (substantially) vertical movement. According to an embodiment of the invention the first holder $1s$ moveable in the said direction.

It is further preferred that the movement in one (preferably the second) direction is a to-and-fro movement, in particular a (substantially) horizontal movement. According to an embodiment of the invention the second and/or the third holder are movable in the said direction.

Again the said movements can be linear movements and it is preferred that they are perpendicular to each other.

The target container is preferably movable over the source container. This saves space and avoids the necessity to make either the first or the third holder, i.e. the distribution apparatus or the source container, movable horizontally.

The subject matter of the invention does not only encompass the above mentioned sample distribution system but also parts thereof. Consequently, all features disclosed in respect of the positioning device and the distribution apparatus in the context of the sample distribution system shall also be disclosed independently in respect of the positioning device and the distribution apparatus respectively.

As described above, the distribution apparatus for distribution of fluid samples is preferably a hand held and/or manually operable device. According to an embodiment of the invention the distribution apparatus is programmable. It could however also be pre-programmed allowing the user to choose between different pre-installed programs and/or to select information pre-stored on the data carrier of the device. It is preferred that one or more items of information are pre-stored on the data carrier, wherein the different items define or determine different operations of the positioning device.

The information determining the operation of the positioning device may take different forms. Firstly, the information could be or comprise operating/control signals that are used for direct control of the positioning device or parts thereof like the actuator, i.e. the information my require no processing or alteration prior to being supplied to the part of the positioning device whose operation is to be controlled. Secondly, the information may be or comprise operating/control routines and/or operating/control programs or program parts. In this form the information would require a microprocessor or the like for processing. Thirdly, the information may be or comprise operating/control parameters that are supplied to a program installed on the positioning device.

Independent of its form the information preferably defines (in respect of the movement of the first, second, and/or third holder) the direction and/or the distance and/or the duration and/or the number and/or the sequence of movements.

The data carrier may be firmly or removably attached to the distribution apparatus. A removable data carrier (e.g. a flash memory card) could be connected to another device (e.g. a computer, hand held electronic device etc.) and the entry, storage, alteration, or selection of information thereon could then be carried out via said device. According to another embodiment, the positioning device may be with an interface (e.g. a connector like a USB-port) for connecting the removable data carrier to the positioning device and thus providing the latter with the necessary information for operation. In this case it is preferred that the information determining the operation of the distribution apparatus is stored on a separate data carrier that remains with the distribution apparatus.

However, it seems preferable that the distribution apparatus comprises a communication interface configured for transmitting the information to the positioning device. The latter is then equipped with a corresponding communication interface for receiving the information. The two interfaces (either wired or wireless) interact to effect transmission of the information. This solution is more user friendly.

A wired communication interface (e.g. in the form of spring contacts) could also be used for charging the battery of the distribution apparatus and it would make pipettor identification easier.

If the above mentioned transmission is of a wireless nature (e.g. Bluetooth) the wrong positioning device, i.e. not the one mounted in the first holder, may control the positioning device. To prevent this, the positioning device may be provided with a user interface (e.g. a button) and a display or a more simple indicator device like one or more light emitting devices (e.g. LEDs, OLEDs etc.). These means then indicate to the user whether the correct distribution apparatus controls the positioning device and give the user the opportunity to confirm the start of the distribution process.

However, there are other ways to achieve the same result, for example the exchange of device IDs (data that identifies a device, e.g. a string of characters) between the distribution apparatus and the positioning device. Nowadays, there exists a plethora of protocols that allow devices to identify themselves to other devices. The transmission of a device ID may be triggered by any means, e.g. actively by the user via the user interface of the distribution apparatus, or by proximity of the devices (e.g. determined by the signal strength of one of the communication interfaces), or upon physical contact of the two devices etc.

According to an embodiment of the invention, the positioning device may then send a confirmation request to the distribution apparatus which provided its device ID and the user may confirm the request via the user interface of the distribution apparatus thus enabling the start of the distribution process.

A simple user interface as described above for the positioning device may also or alternatively be used to indicate other status information like whether a connection to the distribution apparatus has been established, whether the positioning device is ready, busy etc. Furthermore, the positioning device may comprise manual controls like buttons to effect the movement of the holders as described in this document (e.g. for teaching purposes or calibration etc.). However, the main user interface is preferably part of the distribution apparatus.

According to an embodiment of the invention, the positioning device comprises a first holder adapted for (removably) holding a distribution apparatus for distribution of samples and a second holder adapted for holding a target container wherein the first and the second holder are movable relative to each other. Furthermore, the positioning device is configured for receiving information determining and/or controlling the relative movement of the first and second holder from the distribution apparatus.

According to a preferred embodiment of the invention the positioning device comprises
 a first holder adapted for holding (and/or removably mounting therein or thereon) a distribution apparatus for distribution of fluid samples,
 a second holder adapted for holding (and/or removably mounting therein or thereon) a target container,
 preferably a communication interface,
 an actuator for effecting a relative movement of the first holder and the second holder,
wherein the positioning device is configured for receiving (preferably via the communication interface) information from the distribution apparatus determining the operation of (and/or controlling directly or indirectly) the actuator. The information may also determine the operation of (and/or controlling directly or indirectly) other parts of the positioning device.

The holders are each adapted for holding one or more of the described objects (distribution apparatus, target container and —if present—the source container) removably. They are thus adapted for repeated manual mounting and removal of in the said objects by a user. For this purpose the first holder may for instance comprise an opening into which the distribution apparatus can be placed. The second and the third holder are preferably each equipped with a surface (e.g. as part of a carriage) for supporting one or more of the appropriate containers (source/target container), in particular multi well plates. The holders may also be capable of holding different kinds of containers or different kinds of distribution apparatuses (single channel or multi channel pipettors, pipettors with one or more release channels whose position relative to the handle can be changed e.g. as described in US 2009/0274587 A1 etc.).

According to another aspect of the invention the positioning device comprises 1, 2, 3, or more actuators. The movement in the first direction and in the second and/or third direction may thus be effected by different actuators.

The second and/or third holder is preferably movable (at least or only) within a horizontal plane in one, two, or more directions (preferably the second and third direction as described). This may also apply to the first holder. In this case it is preferred that the first holder is also movable up and down. In a preferred embodiment the first holder is movable to and fro, in particular (substantially) horizontally. In addition it is advantageous if it is movable (substantially) perpendicular to the movement direction of the second and/or third holder. For example, the pipettor may move back and forth while one or both containers move left and right. Instead the distribution apparatus may be capable of moving one or more release channels relative to the handle (see for example US 2009/0274587 A1).

According to another embodiment of the invention the distribution apparatus is mounted in the first holder in a manner that allows it to move vertically if it hits an obstacle. It is preferred that the distribution apparatus or the positioning device comprises a sensor that senses the impact when the distribution apparatus hits an obstacle during the distribution process. The signal from the sensor is then used either by the distribution apparatus or directly by the positioning device to effect vertical movement of the first holder.

The invention also encompasses a sample distribution process comprising the steps of:
 entering, storing, altering, assembling, and/or selecting information on a data carrier of a sample distribution apparatus, in particular a hand-held programmable electronic pipettor comprising a user interface, transmitting the information from the distribution apparatus to a positioning device which comprises a first holder adapted for holding the distribution apparatus, a second holder adapted for holding a target container, and an actuator for effecting a relative movement of the first holder and the second holder, using the information for controlling the operation of the actuator and thereby effecting the relative movement of the first holder and the second holder, while the first holder is holding the distribution apparatus and the second holder is holding the target container, and transferring samples from the distribution apparatus to the target container, preferably in between consecutive movements of the first and/or second holder.

However, any sample distribution process using the distribution apparatus, the positioning device, and/or the distribution system described in this document is subject matter of the present invention. It is preferred that they are also used in the sample distribution process as described. The distribution apparatus is preferably capable of controlling the sample distribution system and thus effect the execution of the herein described sample distribution process or parts thereof. Other parts like aspiration of fluid samples may be carried out either automatically or manually.

According to a preferred embodiment of the invention the sample distribution process comprises as steps one or more actions which have been described in the form of capabilities and characteristics of the sample distribution system, the distribution apparatus, and/or the positioning device.

For example, the movability of the first, second, and/or third holder is preferably put into practice as steps of the sample distribution process. Thus the first holder and the second holder are preferably moved relative to each other in a first direction and in a second direction (as described above for the positioning device), samples being transferred from the distribution apparatus and/or the source container to the target container (or from one part of the target container to another part thereof). Preferably the aspiration and release of samples is carried out in between consecutive movements of the first, second, and/or third holder. The target container may be moved over the source container. Furthermore, the first holder and the second holder may be moved (preferably linearly) relative to each other in a third direction which is preferably (substantially) perpendicular to the first and the second direction. If the positioning device comprises a third holder for holding a source container, the first holder and the second holder and/or the first holder and the third holder are preferably moved relative to each other in a first direction and in a second direction (as described above for the positioning device) etc.

In another aspect of the invention, the first, second and/or third holder is loaded manually before the distribution process. It is further preferred that the user loads and ejects the tips (if the distribution apparatus is a pipettor) manually. Thus the positioning device needs not be capable of carrying out the said actions which allows for an inexpensive design of the device.

It is preferred that the information is entered, stored, altered, selected and/or assembled before or after the distribution apparatus has been removably mounted in or on the first holder and/or before or after the data carrier has been connected to the distribution apparatus (if the data carrier is removable).

Entry, storage, alteration, selection, and/or assembly of the information are preferably done manually via the user interface of the distribution apparatus.

It is further preferred that the distribution process comprises (e.g. at least 2, 4, 6, 8, or 10) movements with different starting and/or end positions (the starting- and end-positions being relative positions e.g. of the first and second holder or of the first and third holder). According to an alternative definition, the distribution apparatus is moved over (e.g. at least 2, 4, 6, 8, or 10) different parts of the source and/or target container (e.g. different wells of a multi well plate). Preferably, samples are aspirated or released once the distribution apparatus has reached the said positions above the source or target container ("movement" of the distribution apparatus in this context is to be understood as a change in its position relative to the source and/or target container).

The volumes of fluid aspirated and/or released may be different for different positions and parts of the source and/or target container respectively since the sample distribution process may be a serial dilution process or another process that requires different parts of the target container (e.g. different wells of a multi well plate) to be filled with different volumes or differently composed volumes of fluid.

It is preferred that the distribution apparatus, in particular the pipettor, governs its own movement by means of the positioning device.

According to another preferred embodiment the control of the positioning device in particular its movements and/or the operation of the actuator(s) of the positioning device, are entirely governed by the distribution apparatus.

DETAILED DESCRIPTION OF THE DRAWINGS

Figure 1A:
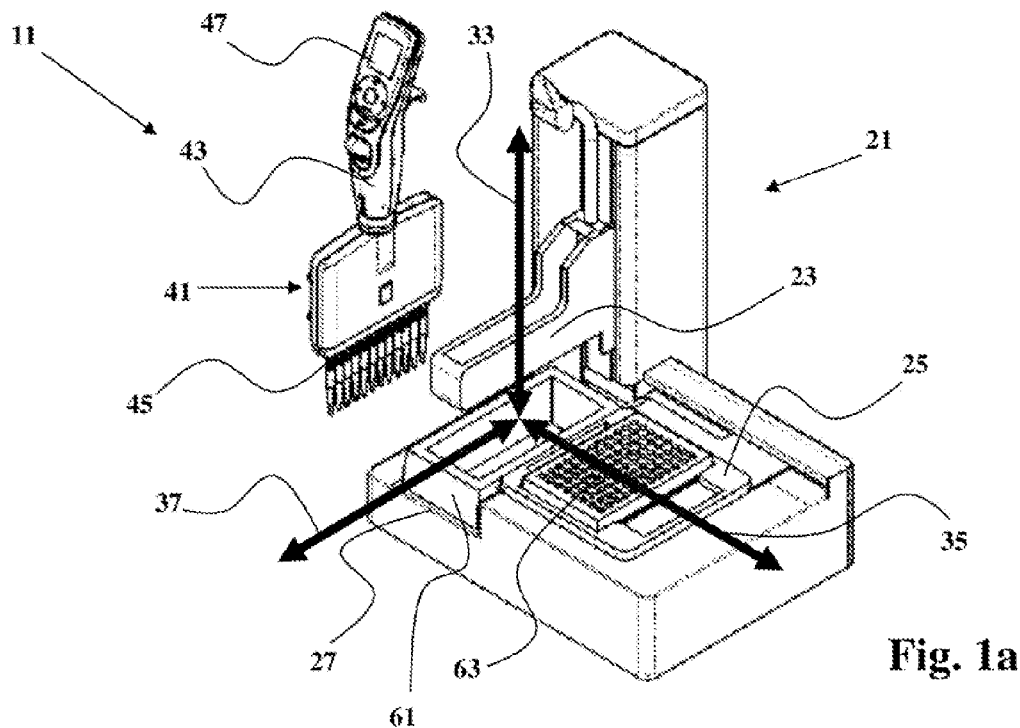
FIG. 1a is a perspective view of a liquid sample distribution system with a distribution apparatus (a hand held programmable electronic pipette) and a positioning device, wherein the distribution apparatus is not mounted in the positioning device.
Figure 1B:
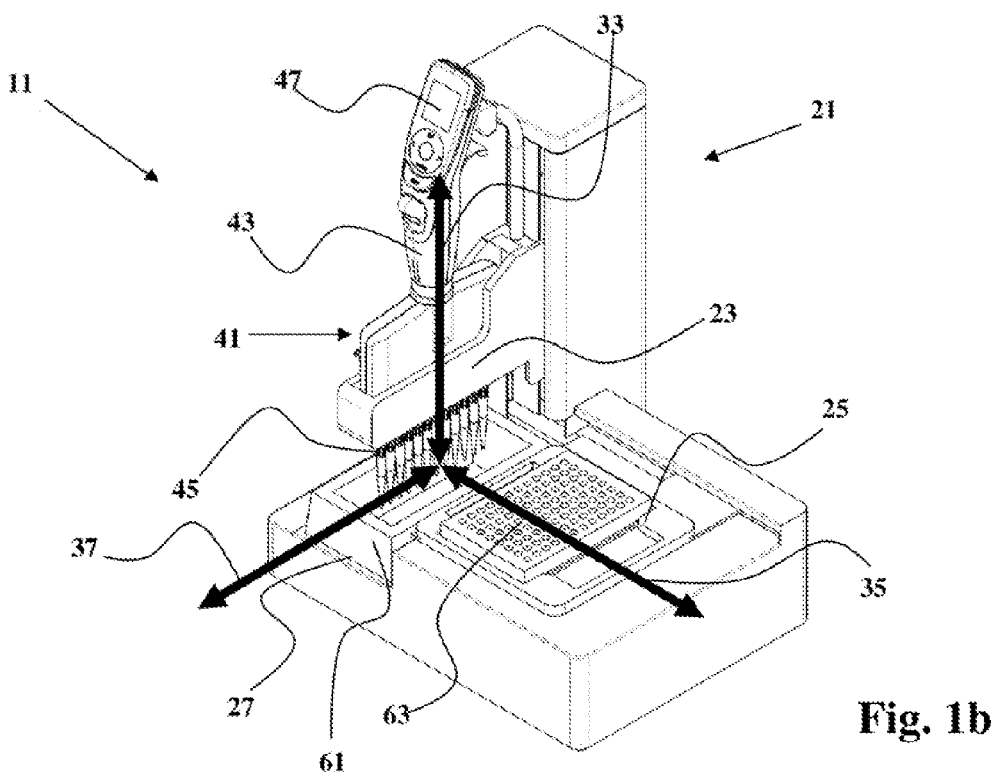
FIG. 1b is a perspective view of the liquid sample distribution system of FIG. 1a wherein the distribution apparatus is mounted in the positioning device.

FIGS. 1a and 1b show an embodiment of a sample distribution system 11 according to the invention. It comprises two main components, the first being a distribution apparatus 41 and the second being a positioning device 21. In FIG. 1b the distribution apparatus 41 is removably mounted in a holder 23 of the positioning device 21 whereas FIG. 1a shows the distribution apparatus 41 and the positioning device 21 separately.

Preferably, the distribution apparatus 41 is a hand held pipettor. Pipettors 41 of this kind are known in the art mainly as laboratory tools for the transfer of measured amounts of fluids from a source container (e.g. a reservoir) to a target container (e.g. a multi well plate). They normally comprise a handle 43 for holding the pipettor 41 during sample distribution and one or more release channels 45 for aspirating and releasing fluid samples. The controls for effecting aspiration and release are located on the handle 43 for easy access by the fingers of the hand holding the pipettor 41. The tips of the release channels 45 are cylindrical and tapered. They have a small hole through which the liquid is aspirated and released respectively and a bigger hole on the opposite end for connection with the distribution apparatus. In order to avoid contamination they are replaceable. Manual operation of such hand held distribution apparatuses 41 normally includes the steps of bringing the tips into contact with a liquid in a source container, aspirating a predetermined volume thereof, moving the distribution apparatus manually to a target container (including lifting the entire distribution apparatus), and releasing all or a predetermined part of the aspirated liquid into the target container.

The second main, component of the sample distribution system 11, namely the positioning device 21, is designed for effecting a relative movement of the pipettor 41, the source container 61, and the target container 63. Thereby the same result is achieved as with the above mentioned manual operation of the pipettor 41. More generally speaking, the positioning device 21 can effect a relative movement of the pipettor 41 and the source container 61 and/or a relative moment of the pipettor 41 and the target container 63. Thereby, liquid samples can be transferred from the source container 61 to the target container 63 or (in sequence) to different predetermined parts of the target container 63. For this purpose the positioning device 21 comprises a fist holder 23 to (or into) which the pipettor 41 can be (removably) mounted (e.g. via click-on connection, snap-in or just by hanging it on the holder etc.). In addition there is a second holder 25 on which the target container 63 can be placed and (optionally) a third holder 27 for holding a source container 61. In the example of FIGS. 1a and 1b the third holder 27 is immovable while the second holder 25 can move horizontally in a second direction 35. It is configured for sliding over the source container 61 which saves space and avoids the necessity to move the source container 61 or the distribution apparatus 41 in the second direction 35. The first holder 23 configured for holding the pipettor 41 is movable into a first direction 33 which is vertical. Thus the positioning device 21 can in a first step move the first holder 23 holding the pipettor 41 down until the tips of the release channels 45 are immersed in the liquid present in the source container 61 (reservoir). In a second step a measured amount of liquid is aspirated. The third step consists of the first holder 23 being moved up whereby the tips of the release channels are lifted out of the source container 61. In a fourth step the second holder 25 holding the target container 63 is moved between the pipettor 41 and the source container 61. The target container 63 in this example is it plate with a multitude of wells. It may however also be a rack with one or more Eppendorf tubes etc. Once the tips of the release channels 45 are positioned above the predetermined part of the target container 63 (which in this example would be a number of predetermined wells) the samples can be released into the target container 63. Prior to release the first holder 23 may be lowered to bring the tips of the release channels 45 closer to the target container 63 and the wells respectively. The target container 63 may then again be moved in the second direction 35 either to remove the target container 63 from between the pipettor 41 and the source container 61 and to allow the pipettor 41 to be refilled. Alternatively, the target container 63 may be moved in the second direction 35 to position another predetermined part of the target container 63, e.g. other wells, below the tips of the release channels 45 and to then release samples from the pipettor into said wells. These steps may be repeated until all wells are provided with the appropriate amount of liquid. Typical applications for the distribution system described in this document are the filling of target containers (e.g. multi well plates) or serial dilution (e.g. in micro titer plates or deep well plates) in a row or column format. If well plates are used as target containers they preferably have 96 or 384 wells. The movement of the first and second holder 23 and 25 are effected by one or more actuators. Electro motors and in particular stepper motors are preferred. However, there are many different kinds of actuators that are suitable for the task of moving the holders (pneumatic, hydraulic or magnetic actuators, piezo elements etc.). The actuator and thus the movement of the holders 23 and 25 is controlled by the distribution apparatus, i.e. the pipettor 41. Also, the operation of the distribution apparatus 41 itself, including the uptake and release of fluid, is controlled by the distribution apparatus 41. For this purpose the pipettor 41 comprises a non-volatile data carrier, e.g. a flash memory chip, on which information is stored that determines the operation of the actuator. The information is provided to the positioning device 21 via a communication interface that connects the pipettor 41 and the positioning device 21. The communication interface may be a wired interface with a connector on the first holder 23 and a corresponding connector on the pipettor 41 which come into contact when the pipetor is mounted in the first holder 23. However, it is preferred that the communication interface is a wireless interface (e.g. Bluetooth, WLAN etc.). The data carrier is firmly or removably attached to the pipettor 41. The storing of the information on the data carrier may be effected before ore while the pipettor 41 is mounted in the first holder 23. It is also possible to first store the information on the data carrier and then connect it to the pipettor 41. Furthermore, it is conceivable to transfer the information from a third device (e.g. a computer, mobile electronic device etc.) via a wired or wireless communication interface to the pipettor. However, according to a preferred embodiment the information is entered, altered, or selected manually via, a user interface 47 which is part of the pipettor 41. The user interface preferably has a display as shown in FIGS. 1a and 1b. The display may be a touch screen and/or the pipettor may have additional controls like buttons for the entry, alteration or selection of the information to be transferred to the positioning device 21. The pipettor 41 is preferably programmable and contains a microprocessor. The programs may provide a graphical user interface on the display that allows the user to enter, select, assemble and/or alter the information to be transferred to the positioning device 21 from data previously stored on the data carrier. The information determining the operation of the actuator may define one or more of the above mentioned process steps. In particular it may define one or more positions of the first holder 23 relative to the second and/or third holder 25 and 27, a sequence of such positions, and/or the amount of liquid to be aspirated or released at predefined positions etc.

Figure 2:
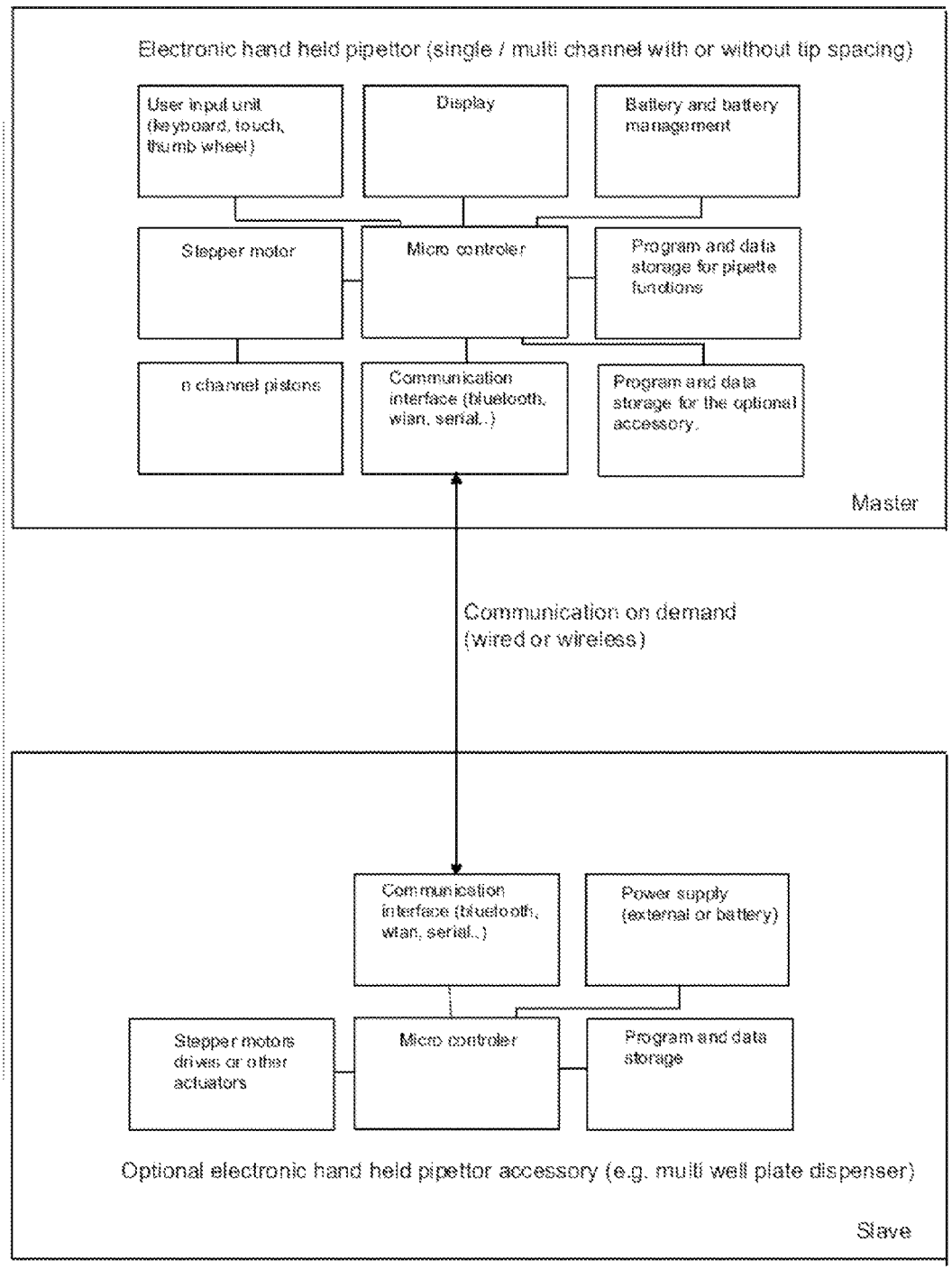
FIG. 2 shows a diagram depicting the components of a sample distribution system.

FIG. 2 shows a diagram depicting components of the distribution apparatus (Master) and the positioning device (Slave) according to a preferred embodiment of the invention The distribution apparatus comprises a micro controller that directly or indirectly controls the different components of the distribution apparatus. Among these components are a power supply, preferably an internal power supply like a battery. Other components are a display and a user input unit, e.g. a keyboard, thumb wheel etc. Furthermore, there is a program and data storage both for pipette functions and for functions of the optional positioning device. The stepper motor that effects movement of one or more pistons that results in aspiration and release of liquid is also under the control of the micro controller. The same applies to a communication interface which might be wired or wireless (e.g. Bluetooth WLAN, a serial interface etc.) and which serves the communication with the positioning device.

The positioning device is also equipped with a micro controller. The latter controls a power supply (external power supply or battery), one or more stepper motors or other actuators for movement of the holders, a program and data storage (for functions of the positioning device), and a communication interface adapted for interaction with the communication interface of the distribution apparatus (Bluetooth, serial interface, WLAN etc.).

NOMENCLATURE 11 sample distribution system
21 positioning device
23 first holder
25 second holder
27 third holder
33 first direction
35 second direction
37 third direction
41 distribution apparatus
43 handle
45 release channels
47 user interface
61 source container/reservoir
63 target container

The invention claimed is:

1. A sample distribution system comprising
a hand-held, programmable, electronic pipettor for hand held distribution of fluid samples, comprising a user interface, a data carrier and a first electronic data communication interface, and
a positioning device comprising a first holder adapted to removably hold the hand-held, electronic pipettor, a second holder adapted to removably hold a target container, at least two electronically controlled motors for effecting a relative movement of the first and the second holders, and a second electronic data communication interface,
wherein the data carrier on the hand-held, electronic pipettor contains information determining some or all of the operation of the electronically controlled motors on the positioning device and the user interface is configured for manual entry, alteration, or selection of the information, part thereof, or a precursor thereof,
the first and the second electronic data communication interfaces are configured for transmission of said information from the hand-held, electronic pipettor to the positioning device, and
the positioning device is configured to receive the information from the electronic pipettor and to control operation of the motors as determined by information received from the electronic pipettor.

2. A positioning device comprising
a first holder adapted to removeably hold a hand-held electronic pipettor for hand held distribution of fluid samples,
a second holder adapted to removeably hold a target container,
an electronic data communication interface,
at least two electronically controlled motors for effecting a relative movement of the first holder and the second holder, and
a slave microcontroller;
wherein the positioning device is configured for receiving via the electronic data communication interface information from the hand-held electronic pipettor, said information being used by the slave microcontroller to control operation of the motors and to move and position the first holder relative to the second holder.

3. A sample distribution process comprising the steps of:
providing a hand-held, programmable electronic pipettor comprising a data carrier,
providing a positioning device comprising a first holder for holding the electronic pipettor, a second holder for holding a target container, and at least two electronically controlled motors for effecting a relative movement of the first and the second holder,
storing information on a data carrier of a hand-held programmable electronic pipettor, said information coordinating the relative movement of the first and second holders on the positioning device and the pipetting action of the electronic pipettor,
placing the hand-held programmable electronic pipettor in a first holder on a positioning device;
transmitting the information electronically from the hand-held, programmable electronic pipettor to the positioning device,
using the transmitted information to control the operation of at least two motors, thereby effecting the relative movement of the first holder holding the electronic pipettor and the second holder holding the target container and
using the information on the data carrier to control operation of the electronic pipettor and transfer fluid samples from the electronic pipettor to the target container.

4. A sample distribution system according to claim 1, wherein
the first holder and the second holder are movable relative to each other in a first and a second direction to allow samples to be transferred from the pipettor to the target container (63),
the movements in the first and the second direction are linear movements,
the first direction is perpendicular to the second direction.

5. A sample distribution system according to claim 1, wherein
the positioning device comprises a third holder for holding a source container,
the first holder and the second holder and/or the first holder and the third holder are moveable relative to each other in a first and a second direction to allow samples to be transferred from the source container to the target container,
the movement in the first and the second direction are linear movements, and
the first direction is perpendicular to the second direction.

6. A sample distribution system according to claim 4 wherein the first holder and the second holder are movable linearly relative to each other in a third direction which is perpendicular to the first and the second direction.

7. A sample distribution system according to claim 1 wherein the first electronic data communication interface and second electronic data communication interface communicate wirelessly.

8. A sample distribution system according to claim 1 wherein the hand-held, electronic pipettor is a multi-channel pipettor.

9. A sample distribution system according to claim 1 wherein the hand-held, electronic pipettor contains a master microcontroller and the positioning device includes a slave microcontroller.

10. A sample distribution system according to claim 1 wherein said electronically controlled motor is a stepper motor.

11. A sample distribution system according to claim 1 wherein the target container is moveable over the source container.

12. A positioning device according to claim 2, wherein
the first holder and the second holder are movable relative to each other in a first direction and in a second direction to allow samples to be transferred from the electronic pipettor to the target container,
wherein the movement in the first direction and the movement in the second direction are linear movements, and
the first direction is perpendicular to the second direction.

13. A positioning device according to claim 2, comprising a third holder for holding a source container, wherein
the first holder and the second holder and/or the first holder and the third holder are moveable relative to each other in a first and a second direction to allow samples to be transferred from the source container to the target container,
the movement in the first and the second direction are linear movements, and
the first direction is perpendicular to the second direction.

14. A hand-held electronic pipettor comprising a data carrier containing information determining the operation of a positioning device according claim 5 and an electronic data communication interface configured for transmitting the information to the positioning device.

15. A hand-held, electronic pipettor according to claim 14, comprising a user interface configured for manual entry, alteration, or selection of the information, part thereof, or a precursor thereof.

16. A positioning device according to claim 12 wherein the first holder and the second holder are movable linearly relative to each other in a third direction which is perpendicular to the first and the second direction.

17. A positioning device according to claim 13 wherein the target container is moveable over the source container.

18. A sample distribution process according to claim 3, wherein
the hand-held programmable electronic pipettor comprises a user interface, and
the information, part thereof, or a precursor thereof is entered, altered, or selected manually via the user interface.

19. A sample distribution process according to claim 3, wherein the step of using the transmitted information to control the operation of the one or more motors, thereby effecting the relative movement of the first holder holding the electronic pipettor and the second holder holding the target container comprises:
moving the first holder and the second holder relative to each other in a first direction and in a second direction,
the movement in the first and the second direction are linear movements, and
the first direction is perpendicular to the second direction.

20. A sample distribution process according to claim 3, wherein
the positioning device comprises a third holder holding a source container,
the first holder and the second holder and/or the first holder and the third holder are moved relative to each other in a first direction and in a second direction, liquid samples being transferred in the process from the source container to the target container,
the movement in the first direction and in the second direction are linear movements, and
the first direction is perpendicular to the second direction.

21. A sample distribution process according to claim 3,
wherein storing, altering and/or selecting the information on the data carrier is done before the distribution apparatus is removably mounted in the first holder.

* * * * *